United States Patent [19]

White, Jr. et al.

[11] 4,185,020
[45] Jan. 22, 1980

[54] 5-(4-NITROPHENYL)-2-FURANMETHANAMINES DERIVATIVES

[75] Inventors: Ralph L. White, Jr.; Chia-Nien Yu, both of Norwich, N.Y.

[73] Assignee: Morton-Norwich Products, Inc., Norwich, N.Y.

[21] Appl. No.: 10,175

[22] Filed: Feb. 7, 1979

[51] Int. Cl.$^2$ .................................................. C07D 307/54
[52] U.S. Cl. .............................. 260/347.3; 260/347.4; 424/285
[58] Field of Search ........................... 260/347.3, 347.4

[56] References Cited

U.S. PATENT DOCUMENTS

| 4,066,672 | 1/1978 | Pelosi ................................. 260/347.7 |
| 4,070,380 | 1/1978 | Pelosi et al. ....................... 260/347.7 |

*Primary Examiner*—Richard Raymond
*Attorney, Agent, or Firm*—Anthony J. Franze

[57] ABSTRACT

Certain 5-(4-nitrophenyl)-2-furanmethanamines are useful as anthelmintic agents.

4 Claims, No Drawings

5-(4-NITROPHENYL)-2-FURANMETHANAMINES DERIVATIVES

This invention is concerned with 5-(4-nitrophenyl)-2-methanamines of the formula:

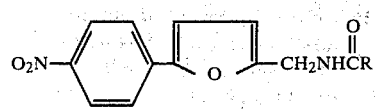

wherein R is ethoxy, methyl or amino.

These compounds are distinguished by their ability to combat helminth infection. When administered by gavage as a suspension in aqueous solution to mice harboring *Ascaris suum* worms, these compounds, in a dose of 100 mg/kg b.i.d. for five days, accomplish about 50-80% reduction of worm burden.

These compounds are readily incorporated in conventional carriers to provide easily administrable compositions such as solutions, tablets, dragees, suspensions, capsules, dispersions and the like using excipients and adjuvants of the compounding art with which there is no incompatibility.

These compounds are easily prepared. Currently, it is preferred to prepare them in accordance with the methods set forth in the following examples.

EXAMPLE I

A. 5-(p-Nitrophenyl)furfuryl alcohol

To a heated suspension of 5-(4-nitrophenyl)-2-furancarboxaldehyde (176 g., 0.8 m.) and 1000 ml of ethanol was added a suspension of sodium borohydride (82 g.) in 1500 ml of ethanol. The solids dissolved and the solution turned very dark. The solution was stirred without external heating until hydrogen ceased to be evolved (22 hours). Upon stirring, the material solidified (pH 9-11). To the suspension was added a 5 percent sulfuric acid solution until the solution was just acidic (600 ml., pH 5-6). The dark mixture was dissolved upon heating at 60°-70° C. for 1 hour. After cooling, the solids were filtered and the filtrate was diluted with water to ppt. the product. The solids were extracted with boiling SDA-32 and the extracts were diluted with water. Total yield of 5-(p-nitrophenyl)-furfuryl alcohol was 150 grams (85%).

B. 5-(p-Nitrophenyl)furfuryl Chloride

In a 5 l R.B. flask were placed 186 g (0.85 mole) of A. and 3.0 l of benzene. To this stirring mixture was added 202 g (1.7 mole) of thionyl chloride all at once. The mixture was heated at reflux for 1.5 hours to a near solution. The near solution was taken to dryness on the water pump. The dark residue was dissolved in 6.0 l of cyclohexane at reflux, treated with Darco and filtered. The filtrate was allowed to stand overnight. Filtration gave 125 g (62%), m.p. 97°-99°, after the collected solid was dried over phosphorus pentoxide in a vacuum desiccator.

For purification, 21 g was dissolved in 500 ml of chloroform and this solution was washed with a 10% solution of sodium bisulfite and dried (Na$_2$SO$_4$). The chloroform solution was concentrated to a yellow solid and recrystallized from 700 ml of cyclohexane to m.p. 97°-99°.

Anal. Calcd. for C$_{11}$H$_8$ClNO$_3$: C, 55.59; H, 3.39; N, 5.90. Found: C, 55.78; H, 3.36; N, 5.90.

C. 5-(p-Nitrophenyl)furfurylamine Hydrochloride

To B. (238 g, 1.0 mole) in 2.0 liters of chloroform was added a suspension of hexamethylenetetramine (140 g, 1.0 mole) in 1.0 l of chloroform over 15 minutes. The hexamine salt began forming within an hour. The salt was collected after stirring for 24 hours without heating and was washed with ether and air-dried.

The salt (325 g, crude) was hydrolyzed in two separate runs. To 162 g was added 2,750 ml ethanol and 1,500 ml of concentrated hydrochloric acid. The mixture was heated on a steam bath for one hour and then cooled to yield yellow solid. From two runs was collected a yellow product which was washed with ethanol and then ether to yield 257 g.

A 97 g sample of material was heated to boiling in a mixture of methanol (600 ml), water (2,200 ml), and concentrated hydrochloric acid (350 ml). It was filtered, and cooled to yield 45 g of purified product, m.p. 261°-264° (dec.).

Anal. Calcd. for C$_{11}$H$_{10}$N$_2$O$_3$.HCl: C, 51.88; H, 4.35; N, 11.00. Found: C, 51.81; H, 4.48; N, 11.15.

D. Ethyl 2-[5-(p-Nitrophenyl)furfuryl]carbamate

To a suspension of 51 g (0.2 m.) of C. in 1200 ml of pyridine under stirring at room temperature was added dropwise 22 g (0.2 m.) of ethyl chloroformate in about 10 min. The temperature of the mixture rose from 25° to 36°. After stirring for an additional 3 hours, it was poured onto crushed ice. Yellow solid separated gradually and the mixture was further diluted with water and allowed to stand overnight.

The mixture was filtered and the solid was washed with water and dried at 60°. The solid was further triturated with ether, filtered and dried. The yield was 27.5 g (47%) m.p. 125°-128°.

Anal. Calcd. for C$_{14}$H$_{14}$N$_2$O$_5$: C, 57.93%; H, 4.86%; N, 9.65%. Found: C, 57.78%; H, 4.99%; N, 9.47%.

EXAMPLE II

N-Acetyl-5-(p-nitrophenyl)furfurylamine

To a suspension of 15.3 g (0.06 m.) of the compound of Example I, C. in 200 ml of pyridine under stirring at room temperature was added dropwise 4.8 g (0.06 m.) of acetyl chloride in about 20 min. Temperature went up from 28° to 38°. The mixture was allowed to stir for 1-½ hours and then poured onto crushed ice. No solid separated on standing. The orange red solution was diluted with large volumes of water to cloud point. Yellow solid separated gradually. The solid was collected, washed well with water and air dried. The yield was 10.5 g (67%). Recrystallization from ethanol gave 4.5 g of purified material, m.p. 149°-151°.

Anal, Calcd. for C$_{13}$H$_{12}$N$_2$O$_4$: C, 59.99%; H, 4.65%; N, 10.77%. Found: C, 60.11%; H, 4.64%; N, 10.76%.

EXAMPLE III

5-p-Nitrophenylfurfurylurea

To a suspension of 5.1 g (0.02 mole) of the compound of Example I, C. in 75 ml of glacial acetic acid under stirring at room temperature was added a solution of 3.5 g (slightly more than 0.04 mole) of potassium cyanate in 25 ml of water. No temperature rise was noticed. The solution was allowed to stir for 1 hour at ambient temperature, and was then warmed on a steam bath for 45 minutes.

After cooling, the solution was poured onto crushed ice and yellow solid separated. The solid was collected, washed with water and air dried. The yield was 3.0 g, m.p. 175°–190°. Twice recrystallization from a mixture of isopropanol and methanol gave the analytical sample, m.p. 209°–211°.

Anal. Calcd. for $C_{12}H_{11}N_3O_4$: C, 55.16%; H, 4.24%; N, 16.09%. Found: C, 55.26%; H, 4.29%; N, 15.83%.

What is claimed is:

1. A compound of the formula:

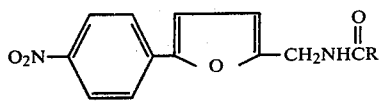

wherein R is ethoxy, methyl or amino.
2. The compound of claim 1 wherein R is ethoxy.
3. The compound of claim 1 wherein R is methyl.
4. The compound of claim 1 wherein R is amino.

* * * * *